United States Patent
Ho et al.

(10) Patent No.: US 8,926,881 B2
(45) Date of Patent: Jan. 6, 2015

(54) SUPER-HYDROPHOBIC HIERARCHICAL STRUCTURES, METHOD OF FORMING THEM AND MEDICAL DEVICES INCORPORATING THEM

(75) Inventors: Audrey Yoke Yee Ho, Crescent (SG); Isabel Rodriguez, Singapore (SG); Hong Yee Low, Botannia (SG); Emma Kim Luong-Van, Singapore (SG); Sriram Natarajan, Hillsborough, NJ (US); Noha Elmouelhi, Randolph, NJ (US); Kevin Cooper, Flemington, NJ (US); Chee Tiong Lim, Singapore (SG)

(73) Assignees: Depuy Synthes Products, LLC, Raynham, MA (US); Agency for Science, Technology and Research, Connexis (SG)

( * ) Notice: Subject to any disclaimer, the term of this patent is extended or adjusted under 35 U.S.C. 154(b) by 0 days.

(21) Appl. No.: 13/441,496

(22) Filed: Apr. 6, 2012

(65) Prior Publication Data
US 2013/0266761 A1    Oct. 10, 2013

(51) Int. Cl.
*B32B 3/30* (2006.01)
(52) U.S. Cl.
USPC .......................... 264/293; 264/219; 264/334
(58) Field of Classification Search
USPC ........................................ 264/219, 293, 334
See application file for complete search history.

(56) References Cited

U.S. PATENT DOCUMENTS

| | | | |
|---|---|---|---|
| 4,256,693 A | 3/1981 | Kondo et al. | |
| 4,464,254 A | 8/1984 | Dojki et al. | |
| 4,557,264 A | 12/1985 | Hinsch | |
| 4,753,776 A | 6/1988 | Hillman et al. | |
| 4,911,165 A | 3/1990 | Lennard et al. | |
| 5,011,494 A | 4/1991 | von Recum et al. | |
| 5,176,692 A | 1/1993 | Wilk et al. | |
| 5,246,451 A | 9/1993 | Trescony et al. | |
| 5,246,666 A | 9/1993 | Vogler et al. | |
| 5,324,519 A | 6/1994 | Dunn et al. | |
| 5,344,611 A | 9/1994 | Vogler et al. | |
| 5,455,009 A | 10/1995 | Vogler et al. | |

(Continued)

FOREIGN PATENT DOCUMENTS

| | | |
|---|---|---|
| DE | 4126877 C1 | 11/1992 |
| DE | 19832634 A1 | 1/2000 |

(Continued)

OTHER PUBLICATIONS

Yuwon Lee et al., "Fabrication of Hierarchical Structures on a Polymer Surface to Mimic Natural Superhydrophobic Surfaces", Advanced Materials, vol. 19, pp. 2330-2335 (2007).

(Continued)

*Primary Examiner* — Jeffrey Wollschlager
*Assistant Examiner* — Stella Yi
(74) *Attorney, Agent, or Firm* — Roberts Mlotkowski Safran & Cole, P.C.

(57) ABSTRACT

Synthetic polymer substrates comprising a hierarchical surface structure of multiple domes and multiple pillars on said domes, wherein said substrate is a synthetic polymer film, said domes have diameters in the range from about 5 μm to about 400 μm, heights in the range from about 2.5 μm and about 500 μm, and said pillars have diameters in the range from about 20 nm to about 5 μm and aspect ratios of from about 2 to about 50, and methods of making and using them.

16 Claims, 2 Drawing Sheets

(56) References Cited

U.S. PATENT DOCUMENTS

| | | | |
|---|---|---|---|
| 5,569,272 | A | 10/1996 | Reed et al. |
| 5,723,219 | A | 3/1998 | Kolluri et al. |
| 6,267,772 | B1 | 7/2001 | Mulhauser et al. |
| 6,368,871 | B1 | 4/2002 | Christel et al. |
| 6,403,655 | B1 | 6/2002 | Bezwada et al. |
| 6,485,503 | B2 | 11/2002 | Jacobs et al. |
| 6,638,284 | B1 | 10/2003 | Rousseau et al. |
| 6,720,469 | B1 | 4/2004 | Curtis et al. |
| 6,872,439 | B2 | 3/2005 | Fearing et al. |
| 6,913,697 | B2 | 7/2005 | Lopez et al. |
| 7,074,294 | B2 | 7/2006 | Dubrow |
| 7,195,872 | B2 | 3/2007 | Agrawal et al. |
| 7,331,199 | B2 | 2/2008 | Ory et al. |
| 7,479,318 | B2 | 1/2009 | Jagota et al. |
| 7,745,223 | B2 | 6/2010 | Schubert et al. |
| 7,754,233 | B2 | 7/2010 | Andjelic et al. |
| 7,988,733 | B2 | 8/2011 | Shimp et al. |
| 8,133,484 | B2 | 3/2012 | Preiss-Bloom et al. |
| 2003/0208888 | A1 | 11/2003 | Fearing et al. |
| 2004/0076822 | A1 | 4/2004 | Jagota et al. |
| 2004/0125266 | A1 | 7/2004 | Miyauchi et al. |
| 2005/0106552 | A1 | 5/2005 | Ikeda |
| 2005/0181629 | A1* | 8/2005 | Jagota et al. ............... 438/780 |
| 2006/0005362 | A1 | 1/2006 | Arzt et al. |
| 2006/0034734 | A1 | 2/2006 | Schubert et al. |
| 2006/0078724 | A1* | 4/2006 | Bhushan et al. ............ 428/323 |
| 2006/0154063 | A1 | 7/2006 | Fujihara et al. |
| 2006/0204738 | A1 | 9/2006 | Dubrow et al. |
| 2007/0227967 | A1 | 10/2007 | Sakaino et al. |
| 2007/0299542 | A1 | 12/2007 | Mathisen et al. |
| 2008/0124246 | A1 | 5/2008 | Diaz-Quijada et al. |
| 2008/0217180 | A1 | 9/2008 | Doye et al. |
| 2008/0241512 | A1 | 10/2008 | Boris et al. |
| 2008/0241926 | A1 | 10/2008 | Lee et al. |
| 2008/0280085 | A1 | 11/2008 | Livne |
| 2009/0130372 | A1 | 5/2009 | Fukui et al. |
| 2009/0318843 | A1 | 12/2009 | Van Holten et al. |
| 2010/0098909 | A1 | 4/2010 | Reyssat et al. |
| 2010/0137903 | A1 | 6/2010 | Lee et al. |
| 2011/0021965 | A1 | 1/2011 | Karp et al. |
| 2011/0160869 | A1 | 6/2011 | Duch et al. |
| 2011/0172760 | A1 | 7/2011 | Anderson |
| 2011/0177288 | A1 | 7/2011 | Bhushan et al. |
| 2011/0282444 | A1 | 11/2011 | Liu et al. |
| 2011/0293667 | A1 | 12/2011 | Baksh et al. |
| 2012/0052234 | A1 | 3/2012 | Natarajan et al. |
| 2012/0143228 | A1 | 6/2012 | Natarajan et al. |
| 2012/0251611 | A1 | 10/2012 | Luong-Van et al. |
| 2012/0302427 | A1 | 11/2012 | Elmouelhi et al. |
| 2012/0302465 | A1 | 11/2012 | Elmouelhi et al. |
| 2013/0172927 | A1 | 7/2013 | Natarajan et al. |
| 2013/0206330 | A1 | 8/2013 | Natarajan et al. |
| 2013/0267880 | A1 | 10/2013 | Luong-Van et al. |
| 2013/0288225 | A1 | 10/2013 | Elmouelhi et al. |

FOREIGN PATENT DOCUMENTS

| | | |
|---|---|---|
| EP | 1416303 | 5/2004 |
| JP | 2004-170935 | 6/2004 |
| JP | 2013-226413 A | 11/2013 |
| SG | 193370 A | 10/2013 |
| WO | 0056808 | 9/2000 |
| WO | 03/099160 A1 | 12/2003 |
| WO | 2004/094303 A2 | 11/2004 |
| WO | 2006031197 | 3/2006 |
| WO | 2009/123739 A1 | 4/2008 |
| WO | 2008/076390 A2 | 6/2008 |
| WO | 2008/102620 A1 | 8/2008 |
| WO | 2009022911 A2 | 2/2009 |
| WO | 2009029045 | 3/2009 |
| WO | 2009/067482 A1 | 5/2009 |
| WO | 2010/129641 A1 | 11/2010 |
| WO | 2011/026987 A1 | 3/2011 |
| WO | 2012/102085 A1 | 3/2012 |
| WO | WO 2012/030570 A1 | 3/2012 |
| WO | 2012/871745 A2 | 11/2012 |
| WO | WO 2012/162452 A2 | 11/2012 |
| WO | 2013/116721 A1 | 7/2013 |
| WO | WO 2013/102085 A1 | 7/2013 |
| WO | 2013/163304 A1 | 10/2013 |

OTHER PUBLICATIONS

Kyoung Je Cha et al., "Effect of Replicated Polymeric Substrate with Lotus Surface Structure on Adipose-Derived Stem Cell Behaviors", Macromoleculare Bioscience, vol. 11, pp. 1357-1363 (2011).

Takashi Yanagishita et al., "Anti-Reflection Structures on Lenses by Nanoimprinting Using Ordered Anodic Porous Alumina", Applied Physics Express 2, pp. 022001-1-022001-3 (2009).

Anna J. Schulte et al., "Hierarchically Structured Superhydrophobic Flowers with Low Hysteresis of the Wild Pansy (Viola Tricolor)—New Design Principles for Biomimetic Materials", Beilstein J. Nanotechnol, vol. 2, pp. 228-236 (2011).

Bharat Bhushan et al., "Micro-, Nano- and Hierarchical Structures for Superhydrophobicity, Self-Cleaning and Low Adhesion", Philosophical Transaction of the Royal Society, A (2009) 367, pp. 1631-1672. Downloaded from rsta.royalsocietypublishing.org on Mar. 2, 2012.

Sitti, "High Aspect Ratio Polymer Micro/Nano-Structure Manufacturing using Nanoembossing, Nanomolding and Directed Self-Assmbly", IEEE/ASME Advanced Mechatronics Conference, Kobe, Japan, Jul. 2003 (5 pages).

Tsougeni, et al. "Nano-texturing of poly (methyl methacrylate) polymer using plasma processes and applications in wetting control and protein adsorption", Microelectronic Engineering 86 (2009), pp. 1424-1427.

Vlachopoulou, et al., "Effect of surface nanostructuring of PDMS on wetting properties, hydrophobic recovery and protein adsorption", Microelectronic Engineering 86 (2009), pp. 1321-1324.

Occhiello, et al., "Oxygen-Plasma-Treated Polypropylene Interfaces with Air, Water, and Epoxy Resins: Part 1. Air and Water.", 1991, Journal of Applied Polymer Science, 42, pp. 551-559.

Gerard, et al., "Surface modifications of polypropylene membranes used for blood filtration", 2011, Polymer, 52, pp. 1223-1233.

Ji Yeong Won et al., "The Fabrication of Protein Nano Arrays Using 3-Dimensional Plastic Nanopillar Patterns", Nanoscience and Nanotechnology, vol. 11, pp. 4231-4235 (2011).

Ning Shao et al., "Self-organized Polymer Aggregates with a Biomimetic Hierarchical Structure and its Superhydrophobic Effect", Cell Biochem Biophys, vol. 49, pp. 91-97 (2007).

Bharat Bhushan et al., "Self-Cleaning Efficiency of Artificial Superhydrophobic Surfaces" Langmuir, vol. 25, No. 5, pp. 3240-3248 (2009).

Jun Shi et al., "Towards Bioinspired Superhydrophobic Ply(L-lactiv acid) Surfaces Using Phase Inversion-Based Methods", Bioinspiration & Biomimetics, vol. 3, pp. 1-6 (2008).

Yong Chae Jung et al., "Wetting Behavior of Water and Oil Droplets in Three-Phase Interfaces for Hydrophobicity/philicity and Oleophobicity/philicity", Langmuir, vol. 25 (24), pp. 14165-14173 (2009).

Sriram Natarajan, PCT No. PCT/US2011/048,584 Filed Aug. 22, 2011.

Audrey Yoke Yee Ho, U.S. Appl. No. 13/441,496, filed Apr. 6, 2012.
U.S. Appl. No. 12/871,745, filed Aug. 30, 2010.
U.S. Appl. No. 13/340,331, filed Dec. 29, 2011.
U.S. Appl. No. 13/340,405, filed Dec. 29, 2011.
U.S. Appl. No. 13/435,544, filed Mar. 30, 2012.
U.S. Appl. No. 13/116,721, filed May 26, 2011.
U.S. Appl. No. 13/441,539, filed Apr. 6, 2012.
U.S. Appl. No. 13/458,825, filed Apr. 27, 2012.

Anthony G. Gristina, "Biomaterial-Centered Infection: Microbial Adhesion Versus Tissue Integration", Science, vol. 237, pp. 1588-1595 (1987).

International Search report for International Application No. PCT/US2011/048584 dated Feb. 20, 2012.

International Search report for International Application No. PCT/US2012/072081 dated Mar. 12, 2013.

(56) References Cited

OTHER PUBLICATIONS

Sriram Natarajan, U.S. Appl. No. 12/871,745, filed Aug. 30, 2010.
Noha Elmouelhi, U.S. Appl. No. 13/116,721, filed May 26, 2011.
Sriram Natarajan, U.S. Appl. No. 13/340,331, filed Dec. 29, 2011.
Noha Elmouelhi, U.S. Appl. No. 13/340,405, filed Dec. 29, 2011.
Emma Kim Luong-Van, U.S. Appl. No. 13/435,544, filed Mar. 30, 2012.
Emma Kim Luong-Van, U.S. Appl. No. 13/441,539, filed Apr. 6, 2012.
Noha Elmouelhi, U.S. Appl. No. 13/458,825, filed Apr. 27, 2012.
Sriram Natarajan, U.S. Appl. No. 13/730,259, filed Dec. 28, 2012.
Sriram Natarajan, U.S. Appl. No. 13/841,561, filed Mar. 15, 2013.
Roure, et al., "Force Mapping in Epithelial Cell Migration", pp. 2390-2395, PNAS, Feb. 15, 2005, vol. 102, No. 7.
Oxford Dictionary Online Definition of "Cylinder".
International Search Report for PCT/US2012/039256 dated Mar. 5, 2013.
Wan Y., et al., "Characterization of surface property of poly (lactide-co-glycolide) after oxygen plasma treatment", Biomaterials, Elsevier Science Publishers, vol. 25, No. 19, Aug. 1, 2004, pp. 4777-4783.
Jianhua Wei, et al., "Influence of surface wettability on competitive protein adsorption and initial attachment of osteoblasts; Competitive protein adsorption and initial cell attachment", Biomedical Materials, Institute of Physics Publishing, vol. 4, No. 4, Aug. 1, 2009, p. 45002.
Tsougeni K., et al., "Mechanisms of oxygen plasma nanotexturing of organic polymer surfaces: From stable super hydrophilic to super hydrophobic surfaces", Langmuir, American Chemical Society, vol. 25, No. 19, Oct. 6, 2009, pp. 11748-11759.
Messina G.M.L., et al., "A multitechnique study of preferential protein adsorption on hydrophobic and hydrophilic plasma-modified polymer surfaces", Colloids and Surfaces. B., Biointerfaces, vol. 70, No. 1, Apr. 1, 2009, pp. 76-83.
Chen H. et al., "The effect of surface microtopography of poly (dimethylsiloxane) on protein adsorption, platelet and cell adhesion", Colloids and Surfaces. B., Biointerfaces, vol. 71, No. 2, Jul. 1, 2009, pp. 275-281.
Definition of "Integral", Merriam-Webster Dictionary online, pp. 1-3, Accessed Oct. 15, 2013.
Sriram Natarajan, U.S. Appl. No. 12/871,745 filed Aug. 30, 2010.
Noha Elmouelhi, U.S. Appl. No. 13/116,721 filed May 26, 2011.
Sriram Natarajan, PCT No. PCT/US2011/048584 Filed Aug. 22, 2011.
Sriram Natarajan, U.S. Appl. No. 13/340,331 filed Dec. 29, 2011.
Noha Elmouelhi, U.S. Appl. No. 13/340,405 filed Dec. 29, 2011.
Emma Kim Luong-Van, U.S. Appl. No. 13/435,544 filed Mar. 30, 2012.
Emma Kim Luong-Van, U.S. Appl. No. 13/441,539 filed Apr. 6, 2012.
Noha Elmouelhi, U.S. Appl. No. 13/458,825 filed Apr. 27, 2012.
Noha Elmouelhi, PCT No. PCT/US2012/039256 filed May 12, 2012.
Sriram Natarajan, U.S. Appl. No. 13/730,259 filed Dec. 28, 2012.
Sriram Natarajan, PCT No. PCT/US2012/072081 filed Dec. 28, 2012.
Sriram Natarajan, U.S. Appl. No. 13/841,561 filed Mar. 15, 2013.
Noha Elmouelhi, PCT No. PCT/US2013/038007 filed Apr. 24, 2013.
Audrey Yoke Yee Ho, U.S. Appl. No. 14/139,673 filed Dec. 23, 2013.
S.D. Lee, "Surface Modification of Polypropylene Under Argon and Oxygen-RF-Plasma Conditions", Plasmas and Polymers, vol. 2, No. 3, Sep. 1, 1997, pp. 177-198.
International Search Report for PCT/US2013/038007 dated Jun. 18, 2013.
Saez et al., "Rigidity-driven growth and migration of epithelial cells on microstructured anisotropic substrates", PNAS, vol. 104, No. 20, pp. 8281-8286, May 15, 2007.

\* cited by examiner

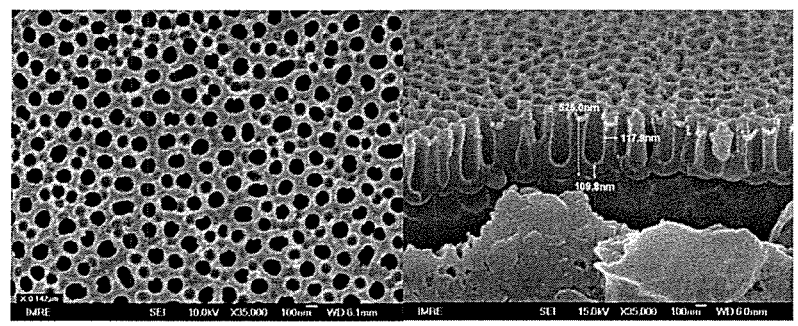
FIG. 1A            FIG. 1B
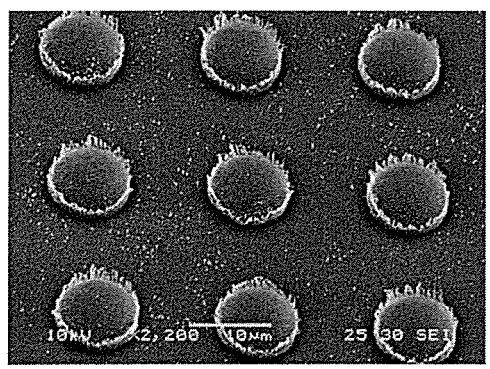    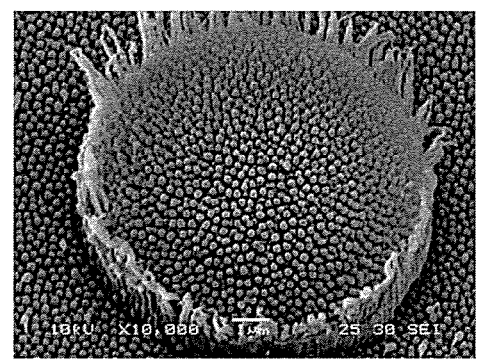
FIG. 2A            FIG. 2B

SUPER-HYDROPHOBIC HIERARCHICAL STRUCTURES, METHOD OF FORMING THEM AND MEDICAL DEVICES INCORPORATING THEM

FIELD OF THE INVENTION

The present invention relates to polymer-based structures having shapes and mechanical properties that induce super-hydrophobicity.

BACKGROUND OF THE INVENTION

It is well known that hydrophobicity may improve the mechanical properties of a surface. One of the crucial surface properties for materials in micro/nanoscale applications is non-wetting or hydrophobicity. Creating hydrophobic surfaces on materials is desirable in some applications, because these surfaces cause water to flow away from the surface, thereby preventing the buildup of liquid on the surface. Hydrophobic surfaces are also desirable due to their self-cleaning properties. These surfaces repel liquids, thereby resulting in liquid and contaminating particles flowing away from the surface.

Wetting is characterized by a contact angle, which is defined as the angle between the solid and liquid surfaces. If a liquid wets the surface, the value of the contact angle is 90° or less (referred to as wetting liquid), whereas if the liquid does not wet the surface (referred to as non-wetting liquid or hydrophobic surface), the value of the contact angle ranges between 90° and 180°. A surface is considered superhydrophobic, if the contact angle has a range of between about 150° to 180°.

Biomimetics has played a role in the development of new surfaces. Biomimetics, which comes from a Greek word "biomimesis" meaning to mimic life, describes the study and simulation of biological objects with desired properties. To that end, scientists have studied natural surfaces that are extremely hydrophobic, in order to reproduce these properties on artificial surfaces. Among these surfaces studied are the leaves of water-repellent plants such as *Nelumbo nucifera* (lotus). At least two surface characteristics are believed to produce water repellent properties on these surfaces. First, the surface of the leaves is usually covered with a range of different waxes made from a mixture of large hydrocarbon molecules, measuring about 1 nm in diameter, that are strongly hydrophobic. Second, the surface is very rough due to so-called papillose epidermal cells, which form asperities or papillae. The surface of the lotus leaf generally has pyramid shaped asperities that are spaced a few μm from one pyramid tip to another pyramid tip. Drops of water substantially contact only the tips or peaks of the pyramids so that the contact area of water to surface is minuscule relative to water drops contacting a micro smooth surface. The reduced contact surface area results in a very low adhesion between the water drops and the micro-rough surface.

Various methodologies have been developed for design and formation of super-hydrophobic surfaces which mimic that of the lotus leaf. For example, U.S. Patent Publication No. 2006/0078724 discloses design criteria for lotus leaf mimetic structures, and suggests a number of methods which could be used to make such structures, including etching and embossing processes, coating processes, shaping processes using appropriately structured molds, polishing processes, photolithography, solvent or vapor deposition, electroplating, electrowetting, plasma processing, warm-water processing, and high temperature sintering. However, no detailed method of formation is disclosed.

In "Fabrication of Hierarchical Structures on a Polymer Surface to Mimic Natural Superhydrophobic Surfaces", *Advanced Materials*, vol. 19, pp. 2330-2335 (2007), Yuwon Lee et al. disclose a fabrication process consisting of three processes: photolithography, aluminum etching/anodization and polymer replication, wherein well-defined microstructure patterns were transferred onto the surface of an aluminum sheet by photolithography using a photoresist and shadow masks, followed by etching and anodizing of the aluminum surface to form a negative, hierarchical replication template, to which was applied a high density polyethylene substrate. The HDPE substrate was forced into the negative template under heat and pressure, and subsequently peeled from the template to produce lotus leaf mimetic hierarchical polymeric structures.

U.S. Patent Publication No. 2008/0217180 discloses a surface comprising a microstructure that reduces adhesion and to a method for producing said microstructure. Microstructures of this type that reduce adhesion are known and are used, for example, to configure self-cleaning surfaces that use the Lotus effect. According to the invention, the surface is produced electrochemically by means of reverse pulse plating, the known microstructure being first produced and a nanostructure that is overlaid on the microstructure is produced at the same time or in a subsequent step.

U.S. Patent Publication No. 2010/0098909 discloses an article having a nanotextured surface with superhydrophobic properties, comprising an array of vertical tabs, formed by photolithography.

In "Effect of Replicated Polymeric Substrate with Lotus Surface Structure on Adipose-Derived Stem Cell Behaviors", *Macromolecular Bioscience*, vol. 11, pp. 1357-1363, Kyoung Je Cha et al. disclose fabrication of polystyrene substrates with lotus leaf surface structures by electroforming nickel onto a natural lotus leaf to form a mold, followed by hot embossing with polystyrene.

U.S. Patent Publication No. 2011/0177288 discloses methods of making superhydrophobic structures comprising depositing a polymer mold onto a silicon surface comprising a plurality of microasperities, removing the polymer mold after the polymer mold has hardened, depositing a liquid epoxy resin into the polymer mold, forming a microstructure with a plurality of microasperities by separating the epoxy resin from the mold after the epoxy resin has solidified, and forming a superhydrophobic structure by depositing a plurality of alkane nanoasperities on the microstructure in the presence of solvent vapor.

It would be desirable to provide a simpler method for formation of hierarchical, biomimetic structures.

SUMMARY OF THE INVENTION

The present invention relates to a method of making a synthetic polymer substrate comprising a hierarchical surface structure of multiple domes and multiple pillars on said domes, comprising forming an array of dome-shaped depressions, each having a diameter and a depth, in a solid template substrate; forming a porous surface on said dome-shaped depressions, wherein said porous surface is formed of a material different from that of said solid template substrate; and contacting said porous surface with a synthetic polymer thermoplastic film under temperature and pressure conditions sufficient to cause said thermoplastic to flow into pores of said porous surface and said dome-shaped depressions to form an imprinted film having said hierarchical surface structure.

In another embodiment, the present invention is directed to a synthetic polymer substrate comprising a hierarchical surface structure of multiple domes and multiple pillars on said domes, wherein said substrate is a synthetic polymer film, said domes have diameters in the range from about 5 μm to about 400 μm, heights in the range from about 2.5 μm to about 500 μm, and said pillars have diameters in the range from about 20 nm to about 5 μm and aspect ratios of from about 2 to about 50.

In a further embodiment, the present invention is directed to a medical device, comprising a substrate having a synthetic polymer film comprising a hierarchical surface structure of multiple domes and multiple pillars on said domes, wherein said synthetic polymer film is a thermoplastic polymer film, said domes have diameters in the range from about 5 μm to about 400 μm, heights in the range from about 2.5 μm to about 500 μm, and said pillars have diameters in the range from about 20 nm to about 5 μm and aspect ratios of from about 2 to about 50.

BRIEF DESCRIPTION OF THE DRAWINGS

FIGS. 1A and 1B show FE-SEM images of top and cross-sectional views, respectively, of a porous anodic alumina (PAA) template prepared by the inventive process.

FIGS. 2A and 2B show FE-SEM images of polypropylene hierarchical lotus leaf-like structures.

DETAILED DESCRIPTION

Figures 3A, 3B, 3C:
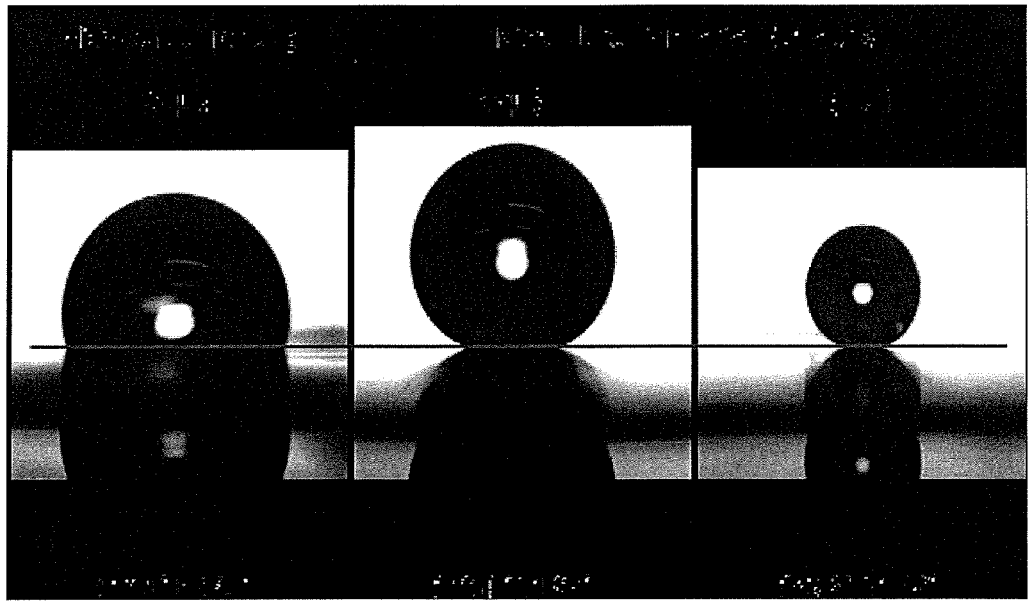
FIGS. 3A-3C show images of water contact angle measurements on domed structures (3A) and on domed-structures having lotus leaf-like topographies (3B, 3C).

Nature has created surface structures that have potential for biological applications. However, these structures are complex mixtures of micro- and nano-sized shapes and features. To fabricate these on polymers of interest is a challenge that needs to be addressed. In order to address this challenge, lotus leaf mimetic surfaces comprising a hierarchical structure of a micrometer-sized dome and a pillared nanosurface have been fabricated by a one step nanoimprinting process on a polymer using a specially prepared hierarchical template.

In one embodiment, the invention is directed to a process to make hierarchical surface features on a polymer substrate. The process involves making a surface with dome-like features by lithographic means on a silicon wafer followed by etching, or by micromachining the dome-like features into a substrate, followed by placing a porous template onto the surface. In either embodiment a polymer film is subsequently pressed into the pores/depressions thereof to form the hierarchical structure onto the surface of the film.

Generally, the process includes forming an array of dome-shaped depressions, each having a diameter and a depth, in a solid template substrate, followed by forming a porous surface on said dome-shaped depressions, wherein said porous surface is formed of a material different from that of said solid template substrate. Subsequently the combined porous surface and solid template substrate is contacted with a synthetic polymer thermoplastic film under temperature and pressure conditions sufficient to cause the thermoplastic polymer to flow into both the pores and the underlying dome-shaped depressions to form an imprinted film having a hierarchical surface structure.

The dome-shaped depressions can have diameters in the range from about 5 μm to about 400 μm, depths in the range from about 2.5 μm to about 500 μm. Advantageously, the pitch (i.e. the center to center distance) between the dome-shaped depressions is approximately equivalent (i.e. on the same order of magnitude) to their chosen diameters. The pores in the porous surface can have diameters in the range from about 20 nm to about 5 μm and aspect ratios of from about 2 to about 50.

Depending on the desired relative dimensions for the hierarchical structure, two different embodiments have been developed for forming the mold.

The initial template can be prepared by standard photolithography and micromachining techniques in silicon. These techniques allow one to produce a wide range of features with high dimensional precision and reproducibility. Different structural features can be used as a first level of hierarchy such as lens, domes, gratings etc with circular or square shapes. The template can be made on or replicated on to other materials like quartz, fuse silica, nickel. Hence, this fabrication approach allows greater flexibility in terms of structural features and/or material for the first level of hierarchy template. On the selected template, an aluminum film is deposited through a sputtering or evaporation processes. The Al film will conform to the features covering the entire surface of the first level template. Upon anodizing of this Al film nano-sized pores are created on the film. The process can create uniform and well-defined height for the hierarchical nanostructures since it uses an Al layer to create these structures, unlike other processes. The anodization process has a natural etch stop on the non-Al substrate.

In a first embodiment of the process, the solid template substrate is a silicon wafer and said dome-shaped depressions are formed by lithography and dry etching. A porous surface is formed by depositing an aluminum film on the dome-shaped depressions and anodizing the aluminum film, which acts to form pores in the aluminum film.

According to this embodiment, the dome-shaped depressions can have diameters in the range from about 10 μm to about 40 μm, depths in the range from about 5 μm to about 20 μm, and the pores can have diameters in the range from about 20 nm to about 500 nm, or even from about 200 nm to about 400 nm, and aspect ratios of from about 2 to about 50, or from about 2 to about 25, or from about 3 to about 25, or from about 2 to about 5. Advantageously, the pores can have an average pore diameter of about 200 nm and an average depth of about 500 nm.

After the polymer film has been flowed into the mold, the process further comprises de-molding the imprinted hierarchical structured film by peeling it from the solid template substrate.

In a second embodiment of the process, the solid template substrate is a metal substrate and said dome-shaped depressions are formed by micromachining. Advantageously, this embodiment of the process does not necessarily require the use of clean room facilities. The process involves initially machining the dome structures in a metal substrate to form the first level of hierarchy. The size limit for this type of machine tooling is in the range of 100 um. The second hierarchical level is achieved using commercial filter membranes. These membranes are typically made of polycarbonate, and have pores running through the thickness of the membranes which are produced using ion track etching. The thickness of the membrane is typically 20 um and the pore widths vary from 0.4-5 um.

The membranes in this embodiment are free standing track etched membranes having pores therein, which are placed on the surface of the machined dome depressions in the solid template substrate, and forced into said dome-shaped depressions along with the thermoplastic polymer film, which is positioned on top of the porous membrane, and under the same temperature and pressure conditions.

According to this embodiment, the dome-shaped depressions can have diameters in the range from about 50 µm to about 400 µm, depths in the range from about 50 µm to about 100 µm, and the pores can have diameters in the range from about 200 nm to about 3 µm, or even from about 400 nm to about 3 µm, and aspect ratios of from about 2 to about 50, or from about 2 to about 25, or from about 3 to about 25. Accordingly, the pores can have diameters in the range from about 0.4 µm to about 3 µm.

As stated above, the method further comprises placing the synthetic polymer thermoplastic film onto said track etched membrane, and applying said temperature and pressure conditions to the combination of the synthetic polymer thermoplastic film and porous membrane, so as to force thermoplastic polymer from a surface of the film into the pores of said free standing track etched membrane, and both of the film and the membrane into the underlying dome shaped depressions in the metal substrate.

Conveniently, the free standing track etched membrane is a polycarbonate filter membrane, and the process further comprises removing the combined polycarbonate filter membrane and polymer film from the mold and dissolving the polycarbonate filter membrane with a solvent, leaving the polymer substrate comprising a hierarchical surface structure. The solvent for the porous membrane should be selected such that it does not affect the polymer film. For example, when the filter membrane is polycarbonate and the synthetic polymer film is polypropylene, tetrachloroethylene is a suitable solvent.

This fabrication process is practical and low cost as it uses machined molds and commercially available porous membranes. However, the process tools limit the fabrication of the hierarchical lotus leaf structures to larger sizes than in the previous process. The dome size and membrane thickness need to be chosen to match. The dome width should be larger by approximately 5 times that of the membrane thickness for the membrane to comply with the dome topography. Likewise, the dome sagitta (depth) should be larger than the thickness of the membrane as otherwise the pillared structures would conceal the dome structure.

The inventive processes described above can be used to make a synthetic polymer substrate, such as one for use on a medical device, comprising a hierarchical surface structure of multiple domes and multiple pillars on said domes, such as wherein the substrate is a synthetic polymer film, the domes can have diameters in the range from about 5 µm to about 400 µm, heights in the range from about 2.5 µm to about 500 µm, and the pillars can have diameters in the range from about 20 nm to about 5 µm and aspect ratios of from about 2 to about 50, or from about 2 to about 25, or even from about 3 to about 25.

Advantageously, the synthetic polymer substrate is a thermoplastic polymer, such as one selected from the group consisting of polypropylene, polycarbonate and polydioxanone, and the domes can have diameters in the range from about 10 µm to about 40 µm, heights in the range from about 5 µm to about 20 µm, and said pillars can have diameters in the range from about 20 nm to about 500 nm, or even from about 200 nm to about 400 nm, and aspect ratios of from about 2 to about 50, or from about 2 to about 25, or from about 3 to about 25, or from about 2 to about 5. Advantageously, the pillars can have average diameters of about 200 nm and average heights of about 500 nm.

Alternatively, when using the micromachining process, the domes can have diameters in the range from about 50 µm to about 400 µm, heights in the range from about 50 µm to about 100 µm, and the pillars can have diameters in the range from about 200 nm to about 3 µm, or even from about 400 nm to about 3 µm, and aspect ratios of from about 2 to about 50, or from about 2 to about 25, or from about 3 to about 25. Accordingly, the pillars can have diameters in the range from about 4 nm to about 3 µm. In this embodiment, the pillars are formed within the pores of a track etched membrane, such as a polycarbonate filter membrane, and the pillars can be essentially cylindrical in shape. The synthetic polymer substrates can have a center-to-center distance (pitch) between the domes which is approximately equivalent to the diameters of the domes.

The synthetic polymer substrates so-formed have a hierarchical structure that renders the surface super-hydrophobic, having static water contact angles of at least about 150°, such as from about 150° to about 165°.

The synthetic polymer substrates so-formed are integrally molded. By integrally molded is meant that the structure is formed in one piece, including both its domes and its pillars, from a mold.

Advantageously, medical devices incorporating the synthetic polymer substrates described above demonstrate benefits such as inhibition of fouling.

The invention is further explained in the description that follows with reference to the drawings illustrating, by way of non-limiting examples, various embodiments of the invention.

EXAMPLE 1

Fabrication Via Hierarchical Template of PAA on Silicon

Silicon molds with domes of 10 um in diameter and depth of 5 um, pitch of 10 µm were fabricated by photolithography followed by plasma etching. The molds were cleaned by corona discharge to remove any organics left from the etching process. The substrates were then coated with a thin film of Ti to serve as an adhesion layer on which a film of aluminum (500 nm in thickness) was sputtered. Subsequently, the aluminum film was anodized in a temperature controlled electrolytic solution of 0.3 M $H_3PO_4$ at constant voltage of 130 V at 2° C. for 1 hour. The pores obtained were then widened by etching the barrier layer formed at the end of the anodization process in a solution of 5 wt % $H_3PO_4$ for 90 min.

FIG. 1A shows a top view and FIG. 1B a cross-sectional view of one of the PAA templates prepared by this process. Typically the pores had an average pore size of 200 nm and a depth of 500 nm. However, pores ranging from 20 nm to 300 nm can be achieved varying the process parameters. The depth of the pores is determined by the anodization time. Typically it was controlled to obtain a pore aspect ratio of 2-5.

Imprinting of Polymer Lotus Leaf-Like Structures

The prepared templates were imprinted into polymers, typically polypropylene (PP), polycarbonate (PC) or polydioxanone (PDO). The templates were initially coated with a fluorosilane release agent through vapor deposition of 1H,1H,2H,2H-perfluorodecyl-trichlorosilane to reduce the surface energy and facilitate the demolding process. The imprinting process was performed using an Obducat nanoimprinter. A free standing film of PP with a thickness of 0.5 mm was placed on top of the template. The template and PP sheet were heated up to 180° C. and a pressure of 60 Bar was applied for 300 s. The polymer-mold assembly was then allowed to cool down to a temperature of 90° C. before the pressure was released and demolding was performed. Demolding was performed by physically peeling off the template. This template prepared with low aspect ratio (AR 2-5) dimensions is reusable as the imprinted polymer readily demolds from the template.

FIGS. 2A (2,200×) and 2B (10,000×) show an example of hierarchical lotus leaf-like structures fabricated in PP. The synthetic structure includes 10 um dome structures with a sagittal (depth) of 5 um and pitch of 20 μm as first level of hierarchy and 200 nm pillar, 500 nm in depth as second level. In FIG. 2 there can be seen elongated pillar structures at the edges of the domes. This elongation takes place due to the pulling force for demolding being applied perpendicular to the pore-pillar structures created on the side walls of the domes. The pulling force caused the elongation of the polymer pillars during demolding probably because the polymer was not completely cooled.

EXAMPLE 2

Fabrication Via Assembly of a Hierarchical Template

Initially, an array of dome-shaped depressions were machined in a metal substrate to form the first level of hierarchy. The size limit for this type of tooling is in the range of 100 um. The second hierarchical level was achieved using commercial filter membranes. These membranes are made typically in polycarbonate, and have pores running through the thickness of the membranes, which are produced using ion track etching. The thickness of the membrane is typically 20 um and the pore width varies from 0.4-5 um.

Imprinting of Polymer Lotus Leaf-Like Structures

A porous polycarbonate filter membrane was placed directly on top of the machined, dome-shaped depressions, the film to be structured was placed on top of the assembly and brought into the imprinter system. Heat (170° C.) and pressure (60 Bar) was then applied to force the thermoplastic film polymer into both the underlying dome-shaped depressions and the pores of the filter membrane. After the imprinting and cooling process, the polymer film was released from the metal mold. The PC membrane which, as a result of the process was embedded into the PP polymer, was removed by dissolving it in tetrachloroethylene. This step results in releasing the second level of pillar structures.

EXAMPLE 3

Measurement of Wetting Properties

The contact angle of the lotus leaf-like surfaces was measured. Measurements were done in triplicate with 5 μl and 1 μl size droplets, and are depicted in FIGS. 3A-3C. The contact angle of a PP surface with 10 um dome structures (113°±2.4°) indicates weak hydrophobicity (FIG. 3A). However, the corresponding lotus leaf-like structures of 10 um domes with 200 nm pillars (FIGS. 3B (5 μl) and 3C (1 μl)) showed a superhydrophobic character, with contact angle readings of 163°±1.5°.

Figures 4A, 4B, 4C:
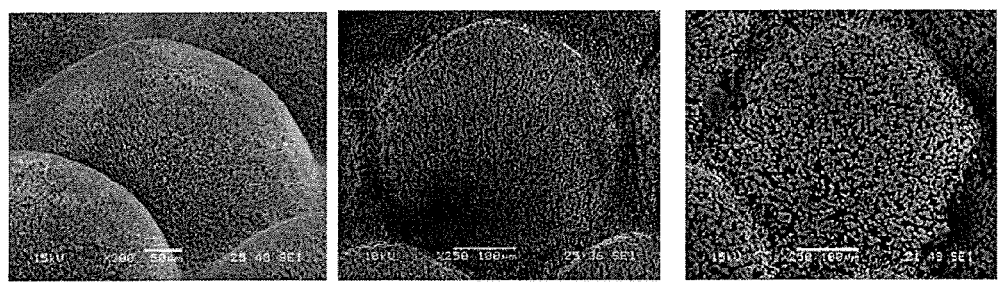
FIGS. 4A-4C show FE-SEM images of lotus leaf-like structures having 400 μm domes and 0.8 μm, 1 μm and 3 μm diameter pillar structures, respectively.

The contact angle of 400 μm PP dome structures having secondary level pillar structures of 0.8, 1 and 3 um diameters are shown in FIGS. 4A-4C, respectively. The contact angle values were lower than the smaller nano-lotus structures in FIGS. 3B and 3C, but nonetheless showed a super-hydrophobic character with contact angle readings above 150°. The contact angle for the structures in FIG. 4A was measured to be 153.1°±4.6°; FIG. 4B was measured to be 150.1°±4.2°; and FIG. 4C was measured to be 151.0°±1.3°.

All patents, test procedures, and other documents cited herein, including priority documents, are fully incorporated by reference to the extent such disclosure is not inconsistent and for all jurisdictions in which such incorporation is permitted.

When numerical lower limits and numerical upper limits are listed herein, ranges from any lower limit to any upper limit are contemplated.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

What is claimed:

1. A method of making a synthetic polymer substrate comprising a hierarchical surface structure of multiple domes and multiple pillars on said domes, comprising:
    forming an array of dome-shaped depressions, each having a diameter and a depth, in a non-aluminum solid template substrate;
    forming a porous surface on said dome-shaped depressions, wherein said porous surface is formed of a material different from that of said solid template substrate; and
    contacting said porous surface with a synthetic polymer thermoplastic film under temperature and pressure conditions sufficient to cause said thermoplastic to flow into pores of said porous surface and said dome-shaped depressions to form an imprinted film having said hierarchical surface structure.

2. The method of claim 1, wherein said solid template substrate is a silicon wafer and said dome-shaped depressions are formed by lithography and dry etching.

3. The method of claim 2, wherein said porous surface is porous anodic alumina, formed by depositing an aluminum film on said dome-shaped depressions and anodizing the aluminum film.

4. The method of claim 1, wherein said dome-shaped depressions have diameters in the range from about 5 μm to about 400 μm, depths in the range from about 2.5 μm and about 500 μm, and pores created in said porous surface have diameters in the range from about 20 nm to about 5 μm and aspect ratios of from about 2 to about 50.

5. The method of claim 2, wherein said dome-shaped depressions have diameters in the range from about 10 μm to about 40 μm, depths in the range from about 5 μm to about 20 μm, and the pores have diameters in the range from about 20 nm to about 500 nm and aspect ratios of from about 2 to about 50.

6. The method of claim 5, wherein said pores have an average pore diameter of about 200 nm and an average depth of about 500 nm.

7. The method of claim 1, wherein said synthetic polymer of said thermoplastic film is selected from the group consisting of polypropylene, polycarbonate and polydioxanone, and the thickness of said film exceeds the depth of said dome-shaped depressions.

8. The method of claim 1, further comprising de-molding said imprinted film from said solid template substrate.

9. The method of claim 1, wherein said solid template substrate is a metal substrate and said dome-shaped depressions are formed by micromachining.

10. The method of claim 9, wherein said porous surface is a free standing track etched membrane having pores therein, which is placed on the surface of said solid template substrate and forced into said dome-shaped depressions under said temperature and pressure conditions.

11. The method of claim 10, wherein said dome-shaped depressions have diameters in the range from about 50 µm to about 400 µm, depths in the range from about 50 µm and about 100 pm, and said pores have diameters in the range from about 200 nm to about 3 µm and aspect ratios of from about 2 to 50.

12. The method of claim 11, wherein said pores have diameters in the range from about 0.4 µm to about 3 µm.

13. The method of claim 10, further comprising placing said synthetic polymer thermoplastic film onto said track etched membrane, and applying said temperature and pressure conditions to said synthetic polymer thermoplastic film so as to force thermoplastic polymer from a surface of said film into the pores of said free standing track etched membrane and into the dome shaped depressions in said metal substrate.

14. The method of claim 10, wherein said free standing track etched membrane is a polycarbonate filter membrane.

15. The method of claim 10, wherein said free standing track etched membrane is a polycarbonate filter membrane, further comprising removing a combined polycarbonate filter membrane and polymer film from said mold and dissolving said polycarbonate filter membrane with a solvent, leaving said polymer substrate comprising a hierarchical surface structure.

16. A method of making a synthetic polymer substrate comprising a hierarchical surface structure of multiple domes and multiple pillars on said domes, comprising:
    forming an array of dome-shaped depressions by micromachining, each having a diameter and a depth, in a metal substrate;
    forming a porous surface on said dome-shaped depressions, wherein said porous surface is a free standing polycarbonate filter membrane having pores therein, which is placed on the surface of said solid template substrate and forced into said dome-shaped depressions under said temperature and pressure conditions;
    contacting said porous surface with a synthetic polymer thermoplastic film under temperature and pressure conditions sufficient to cause said thermoplastic to flow into pores of said porous surface and said dome-shaped depressions to form an imprinted film having said hierarchical surface structure; and
    removing a combined polycarbonate filter membrane and polymer film from said mold and dissolving said polycarbonate filter membrane with a solvent, leaving said polymer substrate comprising a hierarchical surface structure.

* * * * *